US010140707B2

(12) United States Patent
Eusemann

(10) Patent No.: US 10,140,707 B2
(45) Date of Patent: Nov. 27, 2018

(54) SYSTEM TO DETECT FEATURES USING MULTIPLE RECONSTRUCTIONS

(71) Applicant: Siemens Healthcare GmbH, Erlangen (DE)

(72) Inventor: Christian D. Eusemann, Malvern, PA (US)

(73) Assignee: Siemens Healthcare GmbH, Erlangen (DE)

( * ) Notice: Subject to any disclaimer, the term of this patent is extended or adjusted under 35 U.S.C. 154(b) by 61 days.

(21) Appl. No.: 15/378,108

(22) Filed: Dec. 14, 2016

(65) Prior Publication Data

US 2018/0165806 A1   Jun. 14, 2018

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/032* (2013.01); *A61B 6/463* (2013.01); *A61B 6/5217* (2013.01);
(Continued)

(58) Field of Classification Search
CPC ..... G06T 7/0012; G06T 11/00; G06T 11/003; G06T 11/008; G06T 15/20; G06T 2207/10116; G06T 2207/30004; G06T 2207/10072–2207/40084; G06T 2207/10; G06T 2210/41; G06T 2211/40; A61B 6/03; A61B 6/032; A61B 6/463; A61B 6/5217; A61B 6/484; A61B 5/0033; A61B 5/0073; A61B 8/13; A61B 8/15; A61B 17/1703; A61B 2090/376; A61B 2090/3762
See application file for complete search history.

(56) References Cited

U.S. PATENT DOCUMENTS

| 9,478,047 | B2 * | 10/2016 | Seong .................. G06T 3/4053 |
| 2004/0052328 | A1 * | 3/2004 | Sabol .................. G06T 7/0012 378/37 |

(Continued)

OTHER PUBLICATIONS

Extended European Search Report dated May 8, 2018 in EP application No. 17206617.7, 8 pages.
(Continued)

*Primary Examiner* — Jose L Couso

(57) ABSTRACT

Systems and methods to acquire first two-dimensional projection images of a patient volume using first imaging parameters, acquire second two-dimensional projection images of the patient volume acquired using second imaging parameters, generate, using a first image reconstruction technique, a first three-dimensional image based on the first two-dimensional projection images, receive one or more indications of features of the patient volume identified by an operator in the first three-dimensional image, generate, using a second image reconstruction technique, a second three-dimensional image based on the second two-dimensional projection images, perform automated feature extraction on the second three-dimensional image to automatically extract information associated with features of the patient volume, and generate a feature report of the patient volume based on the one or more indications of features and the information associated with features.

17 Claims, 7 Drawing Sheets

(51) Int. Cl.
  *G06T 11/00* (2006.01)
  *G06T 15/20* (2011.01)
  *A61B 6/00* (2006.01)
  *A61B 6/03* (2006.01)
(52) U.S. Cl.
  CPC ........ *G06K 9/00208* (2013.01); *G06T 11/008* (2013.01); *G06T 15/20* (2013.01); *G06K 2209/05* (2013.01); *G06T 2207/10116* (2013.01); *G06T 2207/30004* (2013.01)

(56) References Cited

U.S. PATENT DOCUMENTS

| | | | | |
|---|---|---|---|---|
| 2006/0210131 A1* | 9/2006 | Wheeler, Jr. | .......... | G06T 11/008 382/128 |
| 2007/0052700 A1* | 3/2007 | Wheeler | ............... | G06T 7/0012 345/419 |
| 2007/0189436 A1* | 8/2007 | Goto | ...................... | A61B 6/032 378/4 |
| 2009/0169080 A1* | 7/2009 | Noordhoek | ............. | G06T 5/003 382/131 |
| 2010/0061603 A1* | 3/2010 | Mielekamp | ............ | A61B 6/466 382/128 |
| 2014/0334709 A1* | 11/2014 | Siewerdsen | ........... | G06T 7/0026 382/132 |
| 2015/0154765 A1* | 6/2015 | Huo | ...................... | G06T 11/005 382/132 |
| 2015/0279059 A1* | 10/2015 | Barski | .................. | G06T 15/205 345/427 |
| 2017/0039734 A1* | 2/2017 | Langan | ................. | G06T 11/003 |
| 2018/0032653 A1* | 2/2018 | Aben | .................. | G06F 17/5018 |
| 2018/0033150 A1* | 2/2018 | Lieblich | ................. | G06T 15/08 |

OTHER PUBLICATIONS

James, Alex Pappachen, and Belur V. Dasarathy. "Medical image fusion: A survey of the state of the art." Information Fusion 19 (2014): 4-19.

Calhoun, Vince D., and Tulay Adali. "Feature-based fusion of medical imaging data." IEEE Transactions on Information Technology in Biomedicine 13.5 (2009): 711-720.

* cited by examiner

| Organ | Disease | Reconstruction Type | Kernel | Viewing/Extraction |
|---|---|---|---|---|
| Lung | Cancer | Iterative | Br59 | Extraction |
| Colon | Cancer | Iterative | Br36 | Viewing |
| Colon | Cancer | Iterative | Br40 | Extraction |
| Neuro | Stroke | Iterative | Hr40 | Viewing |
| ... | ... | ... | ... | ... |
| ... | ... | ... | ... | ... |

FIG. 4

| Organ | Disease | Imaging Parameters | Reconstruction Type | Kernel | Viewing/ Extraction |
|---|---|---|---|---|---|
| | | | | | |
| | | | | | |
| | | | | | |
| | | | | | |
| | | | | | |
| | | | | | |

FIG. 7

SYSTEM TO DETECT FEATURES USING MULTIPLE RECONSTRUCTIONS

BACKGROUND

Medical imaging may be used to analyze internal patient anatomy and pathology. This analysis may facilitate a diagnosis, for example by detecting a tumor, leakage after stent placement, iron deposition in the liver, a fracture, etc. More specifically, an image of a tumor may be analyzed to determine features of the tumor (e.g., a size, shape and/or location), and a diagnosis may be determined based in part on these features.

The determination of internal features based on medical images is referred to as feature extraction. Conventional feature extraction systems are limited in their ability to efficiently detect texture, boundaries and/or densities. Efficient systems to improve feature extraction and, as a result, subsequent diagnoses, are desired.

BRIEF DESCRIPTION OF THE DRAWINGS

The construction and usage of embodiments will become readily apparent from consideration of the following specification as illustrated in the accompanying drawings, in which like reference numerals designate like parts, and wherein:

FIG. 4 is a tabular representation of data to determine an image reconstruction technique according to some embodiments;

FIG. 7 is a tabular representation of data to determine imaging parameters and an image reconstruction technique according to some embodiments.

DETAILED DESCRIPTION

The following description is provided to enable any person in the art to make and use the described embodiments and sets forth the best mode contemplated for carrying out the described embodiments. Various modifications, however, will remain readily apparent to those in the art.

Briefly, some embodiments provide improved feature extraction by selectively generating at least one three-dimensional image suited to computer-aided feature extraction and at least one three-dimensional image suited to visual feature extraction, and combining the thus-extracted features.

Figure 1:
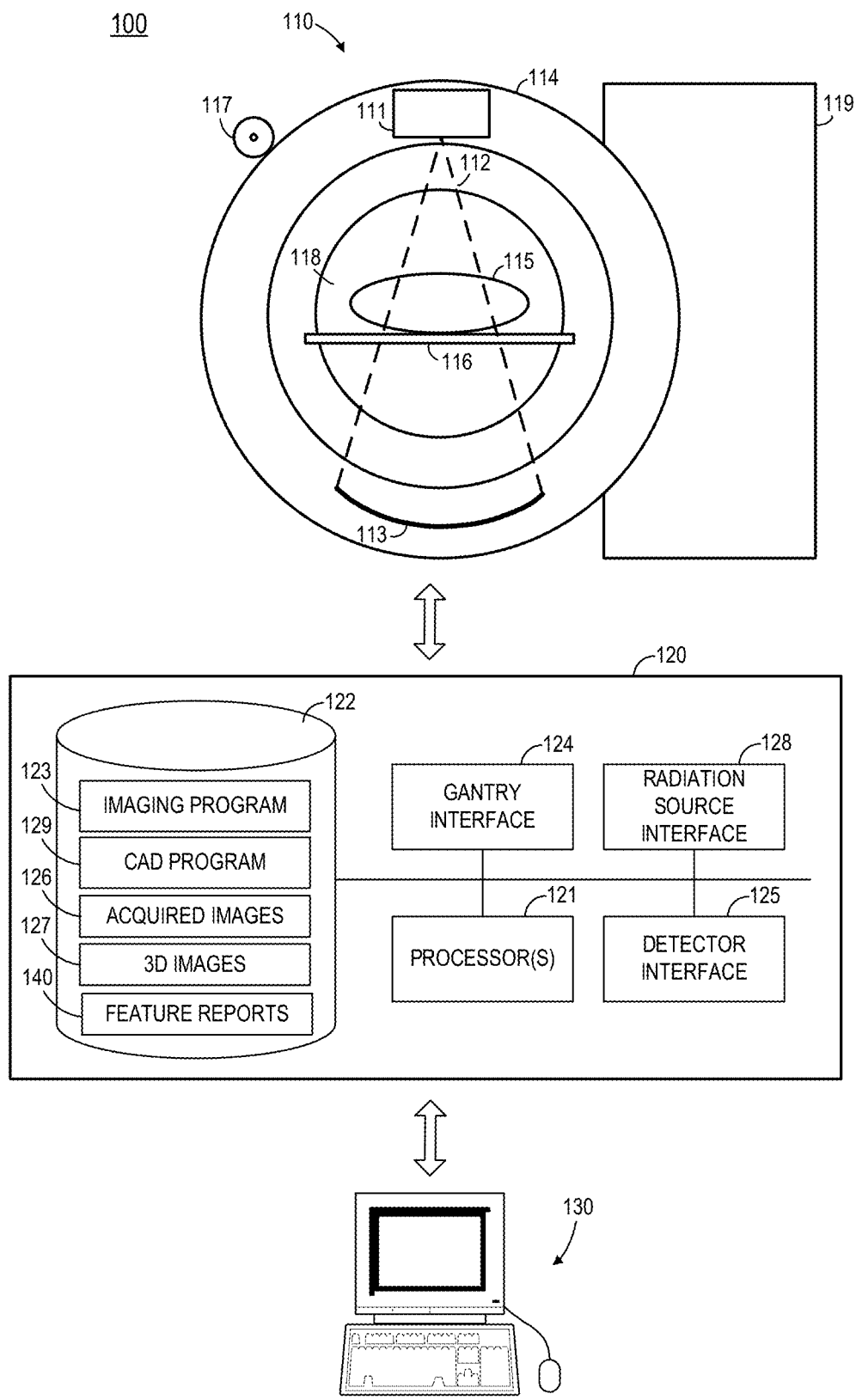
FIG. 1 illustrates an imaging system according to some embodiments.

FIG. 1 illustrates system 100 according to some embodiments. System 100 includes X-ray imaging system 110, control and processing system 120, and operator terminal 130. Generally, and according to some embodiments, X-ray imaging system 110 acquires two-dimensional X-ray images of a patient volume. Control and processing system 120 controls X-ray imaging system 110 and receives the acquired images therefrom. Control and processing system 120 processes the images as described below and provides the processed images and/or information determined based on the processed images to terminal 130 for display thereby. Such processing may be based on user input received by terminal 130 and provided to control and processing system 120 by terminal 130.

Imaging system 110 comprises a CT scanner including X-ray source 111 for emitting X-ray beam 112 toward opposing radiation detector 113. Embodiments are not limited to CT scanners. X-ray source 111 and radiation detector 113 are mounted on gantry 114 such that they may be rotated about a center of rotation of gantry 114 while maintaining the same physical relationship therebetween.

In operation, patient 115 is positioned on bed 116 to place a portion of patient 115 between X-ray source 111 and radiation detector 113. Next, X-ray source 111 and radiation detector 113 are moved to various projection angles with respect to patient 115 by using rotation drive 117 to rotate gantry 114 around cavity 118 in which patient 115 is positioned. At each projection angle, X-ray source 111 is powered by high-voltage generator 119 to transmit X-ray radiation 112 toward detector 113. Detector 113 receives the radiation and produces a set of data (i.e., a raw image) for each projection angle.

X-ray source 111 may comprise any suitable radiation source, including but not limited to a Gigalix™ x-ray tube. In some embodiments, radiation source 112 emits electron, photon or other type of radiation having energies ranging from 50 to 150 keV.

Radiation detector 113 may comprise any system to acquire an image based on received X-ray radiation. In some embodiments, radiation detector 113 uses a scintillator layer and solid-state amorphous silicon photodiodes deployed in a two-dimensional array. The scintillator layer receives photons and generates light in proportion to the intensity of the received photons. The array of photodiodes receives the light and records the intensity of received light as stored electrical charge.

In other embodiments, radiation detector 113 converts received photons to electrical charge without requiring a scintillator layer. The photons are absorbed directly by an array of amorphous selenium photoconductors. The photoconductors convert the photons directly to stored electrical charge.

The charge detected by detector 113 represents radiation intensities at each location of radiation fields produced by X-rays emitted from radiation source 111. The radiation intensity at a particular location of each radiation field represents the attenuative properties of materials lying along a divergent line between detector 113 and the particular location of the radiation field. The set of radiation intensities acquired by radiation detector 113 therefore represents a two-dimensional projection image of these materials.

System 120 may comprise any general-purpose or dedicated computing system. Accordingly, system 120 includes one or more processors 121 configured to execute processor-executable program code to cause system 120 to operate as described herein, and storage device 122 for storing the program code. Storage device 122 may comprise one or more fixed disks, solid-state random access memory, and/or removable media (e.g., a thumb drive) mounted in a corresponding interface (e.g., a USB port).

Storage device 122 stores program code of system control program 123. One or more processors 121 may execute system control program 123 to determine imaging parameters, to rotate gantry 114, to cause radiation source 111 emit radiation at desired energies, and to control detector 113 to acquire images. In this regard, system 120 includes gantry interface 124, detector interface 125 and radiation source interface 128 for communication with elements of system 110. System 120 may also receive input from terminal 130 which may be used to control image acquisition.

Images acquired from system 110 are stored in data storage device 122 as acquired images 126, in DICOM or another data format. Each acquired image 126 may be further associated with details of its acquisition, including but not limited to imaging plane position and angle, imaging position, radiation source-to-detector distance, patient anatomy imaged, patient position, contrast medium bolus injection profile, x-ray tube voltage, image resolution and radiation dosage.

Processor(s) 121 may execute system control program 123 to process acquired images 126. Such processing may generate three-dimensional images 127, which are reconstructed from corresponding sets of two-dimensional images as is known in the art. As will be described below, some embodiments utilize two or more three-dimensional reconstruction techniques to generate two or more three-dimensional images based on a same set of two-dimensional images. Acquired images 126 and/or three-dimensional images 127 may be provided to terminal 130 for display.

Processor(s) 121 may further execute computer-aided diagnosis (i.e., CAD) program 129 to perform computer-aided diagnosis based on acquired images 126 and/or three-dimensional images. Such processing according to some embodiments will be described in detail below. Briefly, computer-aided diagnosis according to some embodiments may identify features within the imaged patient volume and result in generation of a feature report, which may be stored among feature reports 140 of data storage device 122.

Terminal 130 may comprise a display device and an input device coupled to system 120. In some embodiments, terminal 130 is a separate computing device such as, but not limited to, a desktop computer, a laptop computer, a tablet computer, and a smartphone. Terminal 130 displays images and feature reports received from system 120, receives user input for controlling systems 110 and 120, and transmits such user input to system 120.

Each of system 110, system 120 and terminal 130 may include other elements which are necessary for the operation thereof, as well as additional elements for providing functions other than those described herein.

According to the illustrated embodiment, system 120 controls the elements of system 110. System 120 also processes images received from system 110. Moreover, system 120 receives input from terminal 130 and provides processed images to terminal 130. Embodiments are not limited to a single system performing each of these functions. For example, system 110 may be controlled by a dedicated control system, with the acquired images being provided to a separate image processing system over a computer network or via a physical storage medium (e.g., a DVD).

Embodiments are not limited to a CT scanner as described above with respect to FIG. 1. For example, embodiments may employ a dual-arm CT scanner using two radiation sources and corresponding detectors. Such systems may acquire two-dimensional images from two different projection angles substantially simultaneously. Systems employing other imaging modalities (e.g., a magnetic resonance scanner, a positron-emission scanner, etc.) may be used in some embodiments.

Figure 2:
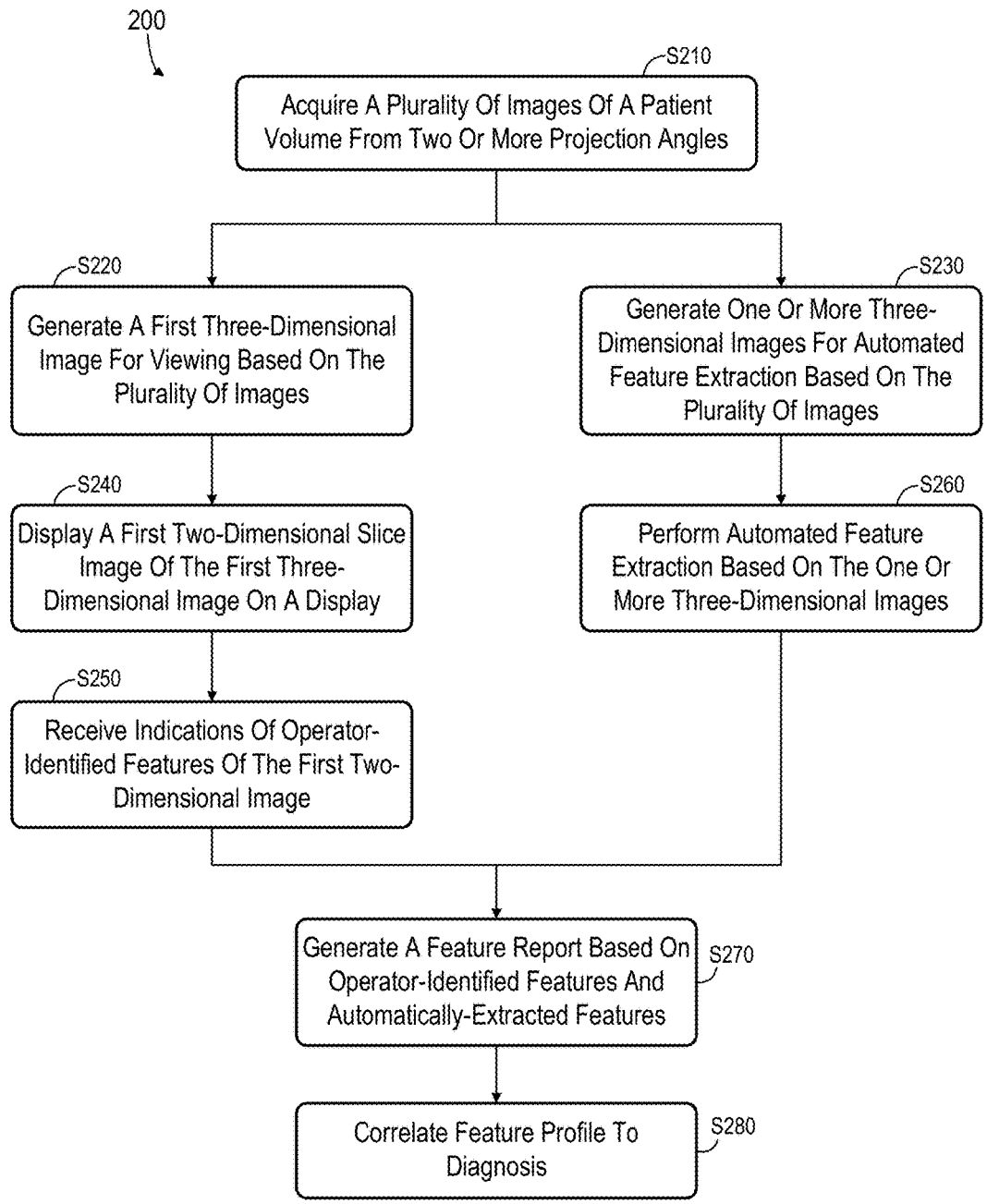
FIG. 2 comprises a flow diagram of a process according to some embodiments.

FIG. 2 comprises a flow diagram of process 200 according to some embodiments. Process 200 and the other processes described herein may be performed using any suitable combination of hardware, software or other means. Software embodying these processes may be stored by any non-transitory tangible medium, including a fixed disk, a floppy disk, a CD, a DVD, a Flash drive, or a magnetic tape. Examples of these processes will be described below with respect to the elements of system 100, but embodiments are not limited thereto.

Initially, at S210, a plurality of images of a patient volume are acquired from two or more projection angles. It will be assumed that, prior to S210, the patient is positioned for imaging according to known techniques. For example, and with reference to the elements of system 100, patient 115 is positioned on table 116 to place a particular volume of patient 115 between radiation source 111 and radiation detector 113. Table 116 may be adjusted to assist in positioning the patient volume as desired. As is known in the art, such positioning may be based on a location of a volume of interest, on positioning markers located on patient 115, on a previously-acquired planning image, and/or on a portal image acquired after an initial positioning of patient 115 on table 116.

According to some embodiments, system 120 executes system control program 123 to instruct system 110 to rotate gantry 114 to position radiation source 111 and radiation detector 113 at each of the plurality of projection angles. At each projection angle, radiation source 111 is powered by generator 119 to emit X-ray radiation toward radiation detector 113. The parameters of the X-ray radiation emission (e.g., projection angles, timing, x-ray tube voltage, dosage) may be specified by a predetermined scan protocol, which may be selected depending upon the volume being scanned. System control program 123 uses these parameters to instruct system 120 to control imaging system 110. Radiation detector 113 receives the emitted radiation and produces a set of data (i.e., a projection image) for each projection angle at S210. The projection images may be received by system 120 and stored among acquired images 126.

Flow then proceeds to S220 and to S230. At S220, a three-dimensional image is generated based on the plurality of two-dimensional images. The three-dimensional image may be generated using any three-dimensional reconstruction techniques that are or become known. The selected reconstruction technique may be a technique which results in a three-dimensional image which is suitable for viewing by human eyes. For example, the reconstruction technique used at S220 may be selected so as to generate a three-dimensional image which, when displayed to an operator in two-dimensional slices, allows the operator to identify certain types of features more readily than if another reconstruction technique was used.

According to some embodiments, the reconstruction technique is an iterative reconstruction technique representing the image characteristics of a sharp kernel. The particular kernel may be specified in the above-mentioned scan protocol. A filtered back-projection or any type of image reconstruction technique may be used at S220, also, for example, using a sharp kernel.

A first two-dimensional image based on the first three-dimensional image is displayed on a display at S240. The first two-dimensional image is a "slice" of the first three-dimensional image as is known in the art. The first two-dimensional image may be displayed to an operator on terminal 130 and/or on another display of a separate computing system. For example, the image may be displayed to an operator (e.g., a radiologist) on a display remote from imaging system 110 several days after acquisition of the plurality of two-dimensional projection images at S210. In this regard, the generation of the three-dimensional image at S220 may occur at any time after acquisition of the two-dimensional images, and may be performed by a computing system separate from computing system 120.

Figure 3:
FIG. 3 illustrates two-dimensional slices of three dimensional images generated based on different reconstruction techniques.

FIG. 3 illustrates two-dimensional slice images based on three-dimensional images which have been generated based on different reconstruction techniques. Image 300 is based on a three-dimensional image which was reconstructed using a reconstruction technique which generates sharp images. Accordingly, image 300 is suitable for viewing, and preferred, by a radiologist. On the other hand, image 350 is a softer image and is a slice of a three-dimensional image which was reconstructed using a reconstruction technique which generates softer images. Image 350 may be more suitable for input to a computer-aided diagnosis system.

Next, at S250, indications of operator-identified features of the first two-dimensional image are received. Operator-identified features may include, but are not limited to, tumor boundaries, tumor surfaces, diseased tissue, abnormal pathology, necrotic regions, tumor enhancement, radionuclide uptake, etc. Systems for identifying such features of a three-dimensional image are known in the art. For example, an operator may manipulate an input device to place electronic marks on the displayed image to denote operator-identified features. The marks may be accompanied by annotations or any other data to provide further information regarding the feature. The electronic marks and any other feature-indicative data are received at S250, for example by system 120. These marks and data may be electronically associated with the first three-dimensional image in any suitable manner (e.g., embedded therein, appended thereto, etc.).

S230 and S260 may proceed in parallel and independently of S220, S240 and S250. One or more three-dimensional images are generated based on the acquired plurality of two-dimensional images at S230. The one or more three-dimensional images are generated using image reconstruction techniques which are intended to generate three-dimensional images suitable for optimized and automated feature extraction using computer-aided diagnosis systems. For example, a three-dimensional image may be generated at S230 based on the plurality of two-dimensional images using an iterative reconstruction technique representing the image characteristics of a soft kernel (e.g., the three-dimensional image from which image 350 is sliced).

Selection of an image reconstruction technique to use at S220 and/or S230 may be based on the volume to be imaged, the features to be extracted, the imaging modality and any other suitable variables. FIG. 4 is a tabular representation of a portion of a data structure 400 which may be used to determine suitable reconstruction techniques for use in S220 and/or S230 according to some embodiments.

Each row of data structure 400 may specify a reconstruction technique (i.e., a reconstruction type and a kernel to be used in conjunction with the reconstruction type) based on an organ to be imaged and a disease type, and may also specify whether the thus-generated three-dimensional image is to be used for viewing or for computer-aided feature extraction. If for viewing, the associated reconstruction technique is to be used at S220. If for feature extraction, the associated reconstruction technique is to be used at S230.

More than one reconstruction technique for feature extraction may correspond to a same combination of organ/disease. In other words, some rows of structure 300 may specify identical combinations of organ/disease but different reconstruction types and/or kernels. A separate three-dimensional image may be generated for each reconstruction technique at S230.

Automated feature extraction is performed at S260 based on the one or more three-dimensional images generated at S230. Any system for performing automated feature extraction that is or becomes known may be used at S260. Several different types of automated feature extraction may be applied to a three-dimensional image generated at S230.

Moreover, different automated feature extraction techniques may be used on different three-dimensional images, depending upon the reconstruction techniques used to generate the different three-dimensional images. For example, if a three-dimensional image is generated at S230 using a soft kernel, then texture extraction may be performed on the three-dimensional image at S260. If another three-dimensional image was generated at S230 using a hard kernel, then boundary extraction may be performed on this three-dimensional image at S260. The type of automated feature extraction to be performed on images generated using a particular reconstruction technique may be stored in a data structure such as structure 300 according to some embodiments.

The output of the feature extraction at S260 may include any type of electronic data indicative of the extracted features. This data, along with the data generated at S250, may be used to generate a feature report at S270. The feature report may comprise the first two-dimensional image and annotations describing the features identified/extracted at S250 and S260. In some embodiments, the data output by S250 and by S260 are not combined and are reviewed separately.

According to some embodiments, the feature report is correlated to a diagnosis at S280. For example, the feature report may conform to the input format of a computer-aided diagnosis application such as CAD program 129. CAD program may execute to generate a diagnosis based on the feature report at S280.

Figure 5:
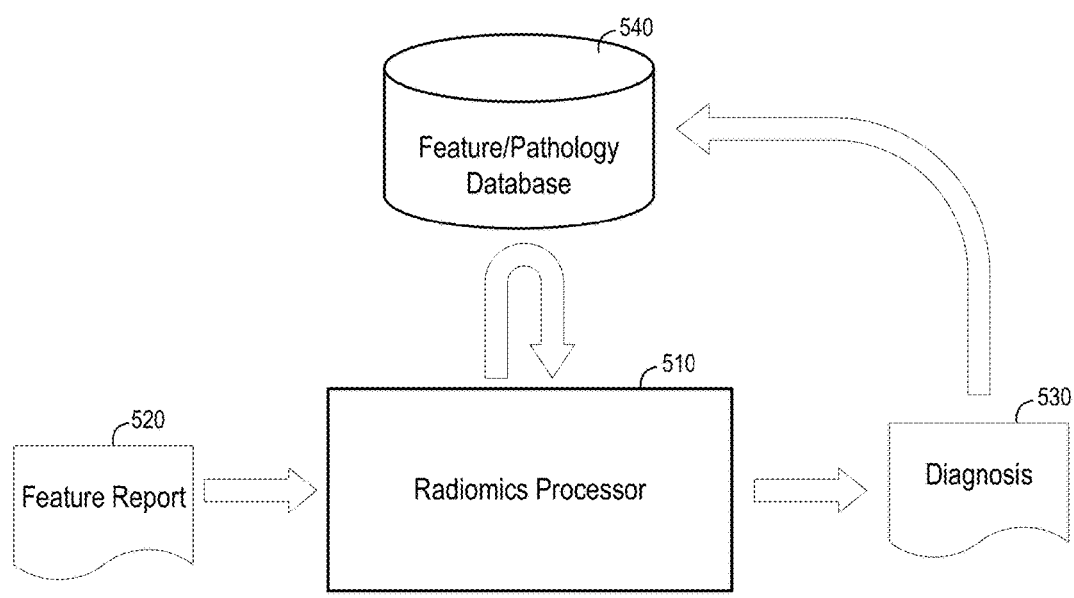
FIG. 5 illustrates determination of a diagnosis according to some embodiments.

FIG. 5 illustrates correlation of a feature report to a diagnosis at S280 according to some embodiments. Radiomics processor 510 may comprise an application executed on computer system 120, an application executed on a separate general-purpose computing device, or a dedicated special-purpose computing device/network. As illustrates, radiomics processor 510 receives features report 520 and generates diagnosis 530 based on data stored in feature/pathology database 540. Moreover, diagnosis 530 may feed back into feature/pathology database to supplement learning algorithms thereof.

Radiomics processor 510 may generate diagnosis 530 using one or more of convolutional neural networks, deep belief networks, recursive neural networks, recurrent neural networks, autoencoders, deep reinforcement learning, decision trees, random forests, Bayes networks, k-means clustering, support vector machines, etc. Accordingly, feature/pathology database 540 may evolve over time as called for by these techniques.

Figure 6:
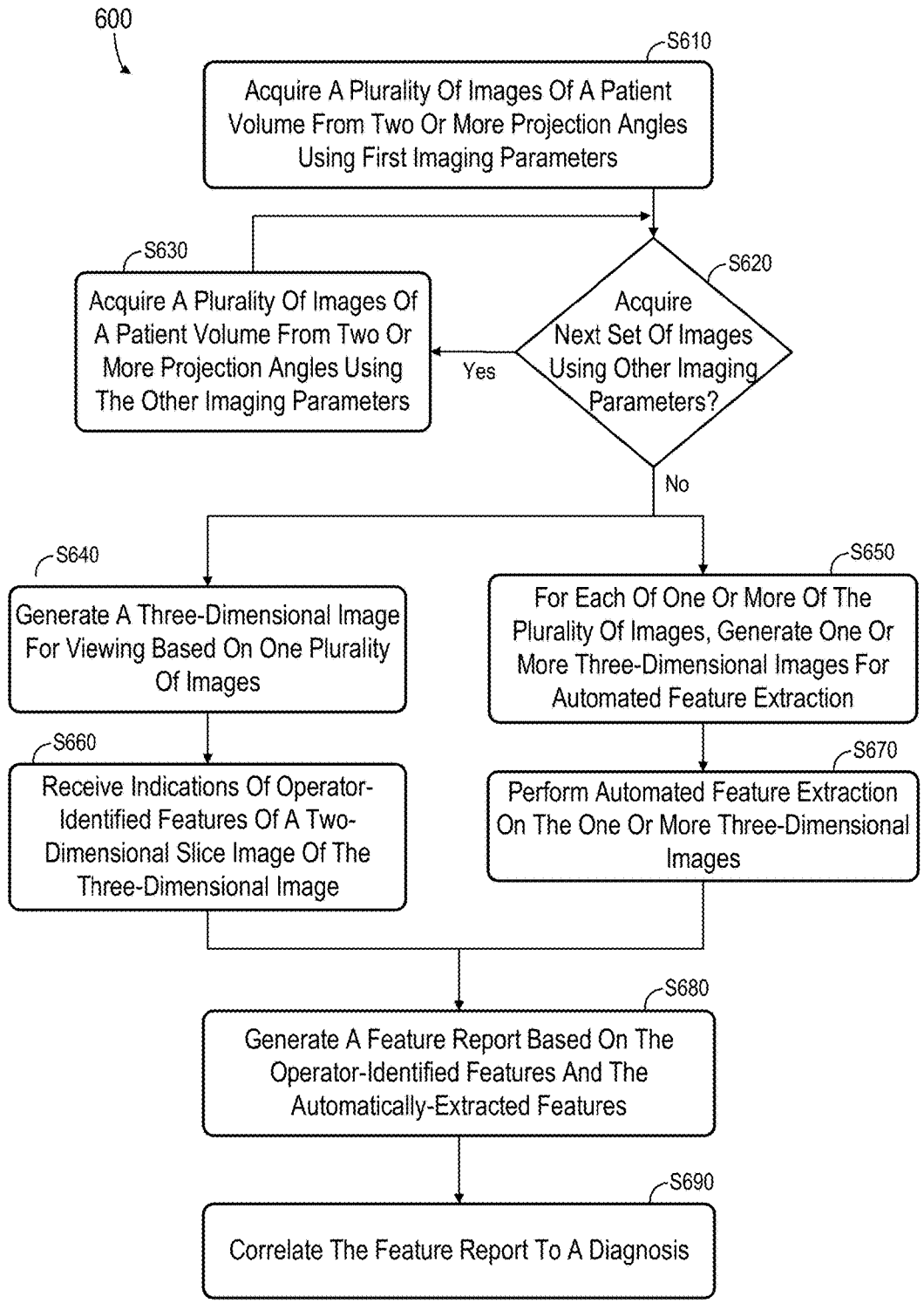
FIG. 6 comprises a flow diagram of a process according to some embodiments.

FIG. 6 comprises a flow diagram of process 600 according to some embodiments. Generally, and unlike process 200 of FIG. 2, process 600 utilizes multiple sets of two-dimensional images, with each set of two-dimensional images being acquired using different imaging parameters.

At S610, a plurality of images of a patient volume are acquired from two or more projection angles. The plurality of images are acquired using a first set of imaging parameters as described above with respect to S210. Next, at S620, it is determined whether to acquire another set of two-dimensional images of the patient volume using other imaging parameters.

For example, the use of other imaging parameters may result in a set of images which is better suited to a particular reconstruction technique and/or feature identification system than the first imaging parameters. If it is determined to acquire a second plurality of images using other imaging parameters, flow proceeds to S630 to acquire the second plurality of images of the patient volume from two or more projection angles using the other imaging parameters. According to some embodiments, the second (and any subsequent) plurality of images is acquired at S630 while the patient remains in substantially a same position as during acquisition of the plurality of images at S610.

In a particular example, the first set of imaging parameters used at S610 may be suited for a particular reconstruction technique in order to generate a three-dimensional image which is optimized for human identification of features. At S620, it may be determined to acquire a second set of images using a second set of imaging parameters which are suited for a particular reconstruction technique in order to generate a three-dimensional image which is optimized for a first automated feature extraction system. Upon returning to S620, it may be determined to acquire a third set of images using a third set of imaging parameters which are suited for a particular reconstruction technique in order to generate a three-dimensional image which is optimized for a second automated feature extraction system.

The determination at S620 may be based on predetermined data such as data stored in data structure 700 of FIG. 7. Data structure 700 may be stored in data storage device 122 and accessed during execution of imaging program 123. Data structure 700 is similar to data structure 400 of FIG. 4, but embodiments are not limited thereto. In contrast to data structure 400, data structure 700 includes a column associating a set of imaging parameters with each combination of organ and disease. Accordingly, each organ/disease pair may be associated with multiple sets of imaging parameters (i.e., with each set of imaging parameters corresponding to a respective row of structure 700), and each set of imaging parameters may in turn be associated with one or more reconstruction techniques. Two or more different sets of imaging parameters may be associated with a same reconstruction technique, and two or more different reconstruction techniques may be associated with a same set of imaging parameters.

Returning to FIG. 6, flow proceeds from S620 to S640 and S650 if the determination at S620 is negative. At S640, a three-dimensional image is generated based on one of the acquired sets of two-dimensional images. The three-dimensional image may be generated using any three-dimensional reconstruction technique which generates a three-dimensional image suitable for human viewing, as described above with respect to S220. A two-dimensional slice image of the image generated at S640 may then be displayed to an operator on terminal 130 and/or on another display of a separate computing system. At S660, indications of operator-identified features of the displayed image are received, as described above with respect to S250.

S650 and S670 may proceed in parallel and independently of S640 and S660. At S650, one or more three-dimensional images are generated based on each of one or more of the sets of acquired images. The one or more three-dimensional images are generated at S650 using image reconstruction techniques which are intended to generate three-dimensional images suitable for automated feature extraction using computer-aided diagnosis systems.

For example, two three-dimensional images may be generated, using two different reconstruction techniques, based on a set of images acquired using first imaging parameters, and one three-dimensional image may be generated, using a same or different reconstruction technique, based on another set of images acquired using second imaging parameters. The number of three-dimensional images to generate based on a set of acquired images, and the reconstruction technique used to generate each three-dimensional image, may be determined based on predetermined data, such as data stored in structure 700.

Automated feature extraction is performed at S670 based on the one or more three-dimensional images generated at S650. Any systems for performing automated feature extraction may be used at S650. As described above with respect to S260, different automated feature extraction techniques may be used on different three-dimensional images, depending upon the different reconstruction techniques used to generate the different three-dimensional images. The type of automated feature extraction to be performed on an image may therefore be determined based on its reconstruction technique and specified by data of a data structure such as structure 700 according to some embodiments.

The output of S660 and S670 is used to generate a feature report at S680, which is correlated to a diagnosis at S690. S680 and S690 may be implemented in any suitable manners, including but not limited to those described with respect to S270 and S280.

According to some embodiments, any known image processing may be applied to the acquired two-dimensional images and the generated three-dimensional images. Such processing may enhance edges, adjust brightness, collimate the field of view, and/or to conform the images to the display properties of the display device of terminal 30. Image processing may include one or more of denoising filters, median filters and low-pass filters.

Those in the art will appreciate that various adaptations and modifications of the above-described embodiments can be configured without departing from the scope and spirit of the claims. Therefore, it is to be understood that the claims may be practiced other than as specifically described herein.

What is claimed is:
1. A system comprising:
an X-ray detector and an X-ray source operable to acquire first two-dimensional images of a patient volume using first imaging parameters and to acquire second two-dimensional images of the patient volume using second imaging parameters;
an interface configured to:
 receive the first two-dimensional projection images;
 receive the second two-dimensional projection images;
a processor configured to execute processor-executable program code that causes the processor to:
 generate, using a first image reconstruction technique, a first three-dimensional image based on the first two-dimensional projection images;
 receive from an input device one or more indications of features of the patient volume in the first three-dimensional image, the indications identified by an operator of the input device;
 generate, using a second image reconstruction technique, a second three-dimensional image based on the second two-dimensional projection images;

perform automated feature extraction on the second three-dimensional image to automatically extract information associated with features of the patient volume;

generate a feature report of the patient volume based on the one or more indications of features and the information associated with features;

a display configured to display a two-dimensional slice image of the first three-dimensional image to the operator.

2. The system according to claim 1, wherein the first image reconstruction technique is optimized to generate a three-dimensional image for viewing; and wherein the second image reconstruction technique is optimized to generate a three-dimensional image for automated feature extraction.

3. The system according to claim 1, the interface further configured to:

receive third two-dimensional projection images of a patient volume acquired using third imaging parameters; and the processor further configured to execute processor-executable program code that causes the processor to:

generate, using a third image reconstruction technique, a third three-dimensional image based on the third two-dimensional projection images; and perform automated feature extraction on the third three-dimensional image to automatically extract second information associated with features of the patient volume, and wherein the feature report of the patient volume is generated based on the one or more indications of features, the information associated with features, and the second information associated with features of the patient volume.

4. The system according to claim 1, the interface further configured to:

receive third two-dimensional projection images of a patient volume acquired using third imaging parameters; and the processor configured further to execute processor-executable program code that causes the processor to:

generate, using the second image reconstruction technique, a third three-dimensional image based on the third two-dimensional projection images; and perform automated feature extraction on the third three-dimensional image to automatically extract second information associated with features of the patient volume, and wherein the feature report of the patient volume is generated based on the one or more indications of features, the information associated with features, and the second information associated with features of the patient volume.

5. The system according to claim 1, the processor further configured to execute processor-executable program code that causes the processor to automatically generate a diagnosis based on the feature report.

6. A method comprising:

acquiring, at an x-ray detector, first two-dimensional projection images of a patient volume using first imaging parameters, the patient volume being exposed to radiation emission from an x-ray source;

acquiring, at the x-ray detector, second two-dimensional projection images of the patient volume acquired using second imaging parameters, the patient volume being exposed to radiation emission from the x-ray source;

generating, using a first image reconstruction technique, a first three-dimensional image based on the first two-dimensional projection images;

receiving, from an input device, one or more indications of features in the first three-dimensional image of the patient volume identified by an operator of the input device;

generating, using a second image reconstruction technique, a second three-dimensional image based on the second two-dimensional projection images;

performing automated feature extraction on the second three-dimensional image to automatically extract information associated with features of the patient volume;

generating a feature report of the patient volume based on the one or more indications of features and the information associated with features; and displaying, on a display, a two-dimensional slice image of the first three-dimensional image to the operator.

7. The method according to claim 6, wherein the first image reconstruction technique is optimized to generate a three-dimensional image for viewing; and wherein the second image reconstruction technique is optimized to generate a three-dimensional image for automated feature extraction.

8. The method according to claim 6, further comprising:

receiving third two-dimensional projection images of a patient volume acquired using third imaging parameters;

generating, using a third image reconstruction technique, a third three-dimensional image based on the third two-dimensional projection images; and performing automated feature extraction on the third three-dimensional image to automatically extract second information associated with features of the patient volume, wherein the feature report of the patient volume is generated based on the one or more indications of features, the information associated with features, and the second information associated with features of the patient volume.

9. The method according to claim 8, wherein the automated feature extraction performed on the third three-dimensional image is different from the automated feature extraction performed on the second three-dimensional image.

10. The method according to claim 6, further comprising:

receiving third two-dimensional projection images of a patient volume acquired using third imaging parameters;

generating, using the second image reconstruction technique, a third three-dimensional image based on the third two-dimensional projection images; and performing automated feature extraction on the third three-dimensional image to automatically extract second information associated with features of the patient volume, wherein the feature report of the patient volume is generated based on the one or more indications of features, the information associated with features, and the second information associated with features of the patient volume.

11. The method according to claim 10, wherein the automated feature extraction performed on the third three-dimensional image is different from the automated feature extraction performed on the second three-dimensional image.

12. The method according to claim 6, further comprising automatically generating a diagnosis based on the feature report.

13. A system comprising:
an interface configured to:
receive first two-dimensional projection images of a patient volume exposed to radiation emission from an x-ray source, each of the first two-dimensional projection images having been acquired at an x-ray detector from a respective one of a plurality of projection angles;
a processor configured to execute processor-executable program code that causes the processor to:
generate, using a first image reconstruction technique, a first three-dimensional image based on the first two-dimensional projection images;
receive at an input device one or more indications of features in the first three-dimensional image of the patient volume identified by an operator of the input device;
generate, using a second image reconstruction technique, a second three-dimensional image based on the first two-dimensional projection images;
perform automated feature extraction on the second three-dimensional image to automatically extract information associated with features of the patient volume;
generate a feature report of the patient volume based on the one or more indications of features and the information associated with features;
a display configured to display a two-dimensional slice of the first three-dimensional image to the operator; and
an input device configured to receive the one or more indications of features from the operator.

14. The system according to claim 13, wherein the first image reconstruction technique is optimized to generate a three-dimensional image for viewing; and
wherein the second image reconstruction technique is optimized to generate a three-dimensional image for automated feature extraction.

15. The system according to claim 13, the processor further configured to execute processor-executable program code that causes the processor to:
generate, using a third image reconstruction technique, a third three-dimensional image based on the first two-dimensional projection images; and
perform automated feature extraction on the third three-dimensional image to automatically extract second information associated with features of the patient volume, and
wherein the feature report of the patient volume is generated based on the one or more indications of features, the information associated with features, and the second information associated with features of the patient volume.

16. The system according to claim 15, wherein the automated feature extraction performed on the third three-dimensional image is different from the automated feature extraction performed on the second three-dimensional image.

17. The system according to claim 12, the processor further configured to execute processor-executable program code that causes the processor to automatically generate a diagnosis based on the feature report.

* * * * *